United States Patent
Dunlavey (10) Patent No.: US 9,955,870 B2
(45) Date of Patent: May 1, 2018

(54) EMERGENCY SERVICES AND INFORMATION BRACELET SYSTEM

(71) Applicant: Allis Dunlavey, New City, NY (US)

(72) Inventor: Allis Dunlavey, New City, NY (US)

(*) Notice: Subject to any disclaimer, the term of this patent is extended or adjusted under 35 U.S.C. 154(b) by 0 days. days.

(21) Appl. No.: 15/631,021

(22) Filed: Jun. 23, 2017

(65) Prior Publication Data

US 2017/0296058 A1    Oct. 19, 2017

Related U.S. Application Data

(63) Continuation-in-part of application No. 15/219,217, filed on Jul. 25, 2016, now abandoned.

(60) Provisional application No. 62/199,948, filed on Jul. 31, 2015.

(51) Int. Cl.
*G08B 1/08* (2006.01)
*A61B 5/00* (2006.01)

(52) U.S. Cl.
CPC .......... *A61B 5/0022* (2013.01); *A61B 5/0002* (2013.01); *A61B 5/0031* (2013.01)

(58) Field of Classification Search
CPC .... A61B 5/0022; A61B 5/0002; A61B 5/0031
USPC .................................................. 340/539.12
See application file for complete search history.

(56) References Cited

U.S. PATENT DOCUMENTS

| | | | | |
|---|---|---|---|---|
| 5,877,742 A | * | 3/1999 | Klink .................... | G06F 19/323 345/685 |
| 2010/0225469 A1 | * | 9/2010 | Yoshioka ........... | G08B 21/0233 340/539.13 |
| 2010/0267361 A1 | * | 10/2010 | Sullivan .................. | G01S 19/17 455/404.2 |
| 2011/0029611 A1 | * | 2/2011 | Hutchison .............. | G06Q 30/02 709/204 |
| 2011/0068926 A1 | * | 3/2011 | Jong .................... | A61B 5/0002 340/573.1 |
| 2011/0298613 A1 | * | 12/2011 | Ben Ayed .......... | A61B 5/02055 340/539.11 |
| 2014/0378853 A1 | * | 12/2014 | McKinney ......... | A61B 5/02438 600/509 |
| 2015/0238835 A1 | * | 8/2015 | Ripken, Jr. ........ | A63B 69/0002 473/451 |
| 2015/0324316 A1 | * | 11/2015 | Moradian ........... | G06F 13/4081 710/303 |
| 2016/0035205 A1 | * | 2/2016 | Messenger ............. | A61B 5/746 340/539.15 |

* cited by examiner

*Primary Examiner* — Kerri McNally
*Assistant Examiner* — Thang Tran
(74) *Attorney, Agent, or Firm* — RG Patent Consulting, LLC; Rachel Gilboy

(57) ABSTRACT

An identifying and monitoring system to be worn at all times that includes a bracelet that can locate lost or missing children, adults, and pets. The bracelet provides emergency personnel with pertinent identifying information including medical history and family contacts. The system includes GPS capabilities and the use of the internet and a web page to upload and download information per each individual bracelet. The bracelet also incorporates a unique locking system that when disengaged from a wearer's wrist an emergency signal and location information is immediately sent to emergency responders.

20 Claims, 4 Drawing Sheets

EMERGENCY SERVICES AND INFORMATION BRACELET SYSTEM

CROSS-REFERENCE TO RELATED APPLICATION

The present application is related to and claims priority from prior provisional application Ser. No. 62/199,948, filed Jul. 31, 2015, and non-provisional application Ser. No. 15/219,217, filed Jul. 25, 2016 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of medical bracelets and more specifically relates to emergency services and information bracelet system readily available and more specifically relates to a waterproof and fireproof, multifaceted identifying and monitoring system to be worn at all times to locate lost or missing children, adults and pets, as well as provide emergency personnel with pertinent identifying information along with medical history and family contact information stored on fire and waterproof paper within the bracelet

2. Description of the Related Art

Keeping their children safe from harm is one of the most paramount concerns of every parent. Whether it is openly discussing, calmly discouraging, or willfully forbidding such harmful acts as smoking, drug use, or unprotected sex, parents seek a myriad of ways to protect their kids in today's fast-paced world. While there are many potentially detrimental forces that can hurt children, parents feel confident that they have control over most of these. However, one of the greatest fears of every mother and father, and one which could render them helpless, is that their child will be lost or abducted.

The Federal Bureau of Investigation estimates that more than 2,000 children are reported missing each day in the United States, adding up to nearly 750,000 children a year who run away from home or are the victims of a family or non-family abduction. Providing a visual to go along with these alarming statistics, bulletin boards in large shopping centers are virtually covered with missing children flyers and posters.

As diligent as parents are in keeping a constant eye on their little ones, children are very curious and energetic by nature. Walking through a mall, strolling along the fairway of an amusement park, or enjoying a day out at a city park provide many attractive distractions that may inspire kids to wander off and investigate. In a split second, a child can be lost in these crowded and busy places. To help parents keep inquisitive children in sight at all times, there are several items on the market that can facilitate constant contact. Very popular in recent years, a child leash has become an alternative to constantly holding a child's hand to keep him from scampering off. Similar in style to a dog leash, one end of this harness is tied to the parent's arm while the other end is secured around the child's wrist.

While these leashes help parents keep active children close by, they can result in chafing of the skin, particularly if a rambunctious child is tethered to it. Additionally, many people see the child leash as inhumane, and are discouraged from using one. In addition, parents have turned to two-way radios and even cellular telephones as means of staying in contact. While these costly items work well for close communication with kids old enough to be responsible for carrying them and using them, they could prove too challenging, and therefore impractical, as a security measure for younger children.

Various attempts have been made to solve the above-mentioned problems such as those found in U.S. Pat. No. 5,877,742 to James Klink; U.S. Pat. No. 6,223,559 to Shelia J. Coleman; and U.S. Pat. No. 6,255,951 to Carlos De La Huerga. This art is representative of medical bracelets. None of the above inventions and patents, taken either singly or in combination, is seen to describe the invention as claimed.

Ideally, a medical bracelet should provide fast emergency service, location, and medical information, and yet, would operate reliably and be manufactured at a modest expense. Thus, a need exists for a reliable emergency services and information bracelet system to avoid the above-mentioned problems.

BRIEF SUMMARY OF THE INVENTION

In view of the foregoing disadvantages inherent in the known medical bracelets art, the present invention provides a novel emergency services and information bracelet system. The general purpose of the present invention, which will be described subsequently in greater detail, is to provide a fast emergency service, location, and medical information.

The emergency service and information bracelet system is a waterproof and fireproof, multifaceted identifying and monitoring system to be worn at all times that can locate lost or missing children, adults, pets and be the Guardian Angel for those who can't speak for themselves. The emergency services and information bracelet system preferably includes identifying information and will permit a parent to sign a permission statement granting emergency personnel to grant life-saving medical treatment to their child or family member when they can't be reached. The design intent of emergency services and information bracelet system is to create a "Multi-Generational Family Commitment" to wear the emergency services and information bracelet system, thus bringing peace-of-mind knowing that all family members can be identified, located quickly and properly cared for, should a tragedy strike. Consumers will take pride in wearing this bracelet knowing that they are indeed, Loved.

The emergency service and information bracelet system is a waterproof and fireproof, multifaceted identifying and monitoring system to be worn at all times that can locate lost or missing children, adults, pets and be the Guardian Angel for those who can't speak for themselves.

The emergency services and information bracelet system has two embodiments. The emergency services and information bracelet system has more than one objective and multiple complimentary parts that work in conjunction with each other to achieve the objective. The first objective of this system is to identify the wearers of the bracelet as belonging to a family or group in the event of a catastrophe. It will provide emergency personnel with pertinent identifying information along with medical history and family contact information stored on fire and waterproof paper within the bracelet. Should a catastrophe or other emergency situation strike, the bracelet will ensure that family members or members of the group are found, identified, and properly treated right away. If the bracelet is taken off the unique safety lock will notify police and parents immediately. The emergency services and information bracelet system will preferably have the universal medical alert symbol which will call 911 for help. All hospital personnel, medical personnel, emergency responders, fire personnel, police, will know to look for this bracelet.

For identification purposes, inside the bracelet would be the wearer's name, address, and phone number written on special paper, as well as any medical conditions and what types of medications, if any, are required, along with emergency contact information including an out of town contact. To assist in viewing this information, a small magnifying glass would be provided. The information is included on paper so that emergency responders do not need to rely on technology, which may not be available due to a tragic event, in order to access the wearer's emergency information. Information can also be easily updated at any time. Importantly, with this information on paper, it could be instantly accessed, saving precious seconds or minutes. A unique safety lock design would be used to fasten the bracelet and hold the informative paper within the unit.

The first embodiment is the emergency bracelet to be worn by a user for emergency services and information and is an emergency bracelet comprising a main body that is adapted to wrap around and be maintained upon a user's wrist. The main body is formed from a material that is waterproof and fireproof and has a power source. The power source is located and attached within the main body and the power source preferably includes a battery member. The power source may include a solar panel adapted to be attached to the outer surface of the main body and electrically attached to the battery member for recharging the battery member.

A first button is attached to the main body and is adapted to activate a GPS system adapted to send location information wirelessly to emergency personnel and a transmitter is located and attached within the main body and is adapted to send information to the GPS system. One example of an application for this system would be the ability of family members to be linked together so that parents are able to keep constant knowledge of the locations of their children through the GPS function. The transmitter includes a frequency generator, an amplifier, and an internal antenna. The piece of paper is adapted to be folded and stored within the main body and is capable of being retrieved by emergency personnel, and the piece of paper contains vital information thereon about the user to be used by the emergency personnel to help aid the user in an emergency. A magnifying glass is included and adapted to be stored within the main body and is capable of being retrieved by the emergency personnel to be used to read the vital information on the piece of paper. A sound generator is attached to the main body and is adapted to create a sound to indicate the need for emergency services.

There is a second button that is attached to the main body also that is adapted to activate the sound generator. The emergency bracelet to be worn by a user for emergency services and information further may comprise a USB flash drive adapted to be stored within the main body that is capable of being retrieved by the emergency personnel which contains vital information thereon about the user to be used by the emergency personnel to help aid the user in an emergency.

In the second embodiment, an emergency system for emergency services may comprise a GPS system and a receiver unit that is adapted to receive information from the GPS system, a central computer network including at least one computer module adapted to receive and process the information from the receiver unit and alert appropriate emergency personnel to a user at a location determined by the GPS system and an emergency bracelet adapted to be worn by the user for providing emergency information. The computer module includes multiple computer modules adapted to link a plurality of users together. The main body is adapted to wrap around and be maintained upon a user's wrist. The main body is formed from a material that is adapted to be water proof and fireproof.

A power source is located and attached within the main body. The power source includes a battery member but may also include a solar panel adapted to be attached to an outer surface of the main body and electrically attached to the battery member for recharging the battery member. There is a first button that is attached to the main body that is adapted to activate the GPS system to send location information wirelessly to emergency personnel via a transmitter. The transmitter is located and attached within the main body and is adapted to send information to the GPS system. The transmitter includes a frequency generator, an amplifier, and an internal antenna. A piece of paper is adapted to be folded and stored within the main body and is capable of being retrieved by the emergency personnel and contains vital information thereon about the user to be used by the emergency personnel to help aid the user in an emergency.

A magnifying glass is adapted to be stored within the main body and is capable of being retrieved by the emergency personnel to be used to read the vital information on the piece of paper. A sound generator is attached to the main body and is adapted to create a sound to indicate the need for emergency services. There is a second button is attached to the main body that is adapted to activate the sound generator. The emergency system for emergency services may further comprise a USB flash drive adapted to be stored within the main body and is capable of being retrieved by the emergency personnel. The USB flash drive contains any necessary vital information thereon about the user that can be used by the emergency personnel to help aid the user in the event of an emergency. The emergency services and information bracelet system (I Am Loved Bracelet) is strongly encouraged for family use, including Special Needs Consumers and Pets. An ever present tool offering peace-of-mind to families and loved ones. The I Am Loved Bracelet system will be a GUARDIAN ANGEL for those who cannot speak for themselves.

The present invention holds significant improvements and serves as an emergency services and information bracelet system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, emergency services and information bracelet system, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a medical bracelets and more particularly to a emergency services and information bracelet system readily available and more specifically relates to a waterproof and fireproof, multifaceted identifying and monitoring system to be worn at all times to locate lost or missing children, adults and pets, as well as provide emergency personnel with pertinent identifying information along with medical history and family contact information stored on fire and waterproof paper within the bracelet Generally speaking, the emergency services and information bracelet system is an identification bracelet system having written and electronic information located within the bracelet and a GPS transmitter for emergency personnel and law enforcement authorities to render aid to the wearer.

The Emergency services and information bracelet system comprises a specially designed to create a "Multi Generational Family Commitment" to wear the emergency services and information bracelet system, thus bringing peace-of-mind knowing that all family members can be identified, located quickly and properly cared for, should a tragedy strike. Consumers will take pride in wearing this bracelet knowing that they are indeed, Loved.

Configured in the form of a fashionable, waterproof and fireproof bracelet sized appropriately for wear by children as well as their parents, grandparents, caregivers, and pets, the emergency services and information bracelet system would offer a transmitting and receiving combination that links all members of the family. The transmitter would be a handy Global Positioning System (GPS) which could enhance the parent's ability to know where the child (or other loved one) is at all times. For instant location, the transmitter would feature a frequency generator, amplifier, and internal antenna. The synched receiver would consist of a tuned frequency and receiver circuit, with location information relayed to a computer, or officials, if necessary.

For identification purposes, inside the emergency services and information bracelet system would be, on special paper, the wearer's name, address, and phone number, as well as any medical conditions, and what medications, if any, are required, along with emergency contact information including an out of town contact. To assist in viewing this information, a small magnifying glass would be provided. The information is included on paper so that emergency responders do not need to rely on technology, which may not be available due to a tragic event, in order to access the wearer's emergency information. Information can also be easily updated at any time. Importantly, with this information on paper, it could be instantly accessed, saving precious seconds or minutes.

A unique safety lock design would be used to fasten the bracelet and hold the informative paper within the unit. The emergency services and information bracelet system would boast an emergency "Angel Button" which when pressed would sound an audible panic alarm. In addition, a universal medical alert symbol button would serve, when pressed, to activate the GPS locator and call 911 for help. (All hospital personnel, medical personnel, emergency responders, fire personnel, police, etc., will know to look for this bracelet.)

The emergency services and information bracelet system could be made available in a variety of colors and styles to appeal to individual tastes. In addition, professional and high-end styles would also be produced. The emergency services and information bracelet system is not just designed for children, but is also for use by any loved one, and is strongly encouraged for family use, including special needs consumers and pets. An ever present tool offering peace-of-mind to families and loved ones, the emergency services and information bracelet system will be a guardian angel for those who cannot speak for themselves.

Figure 1A:
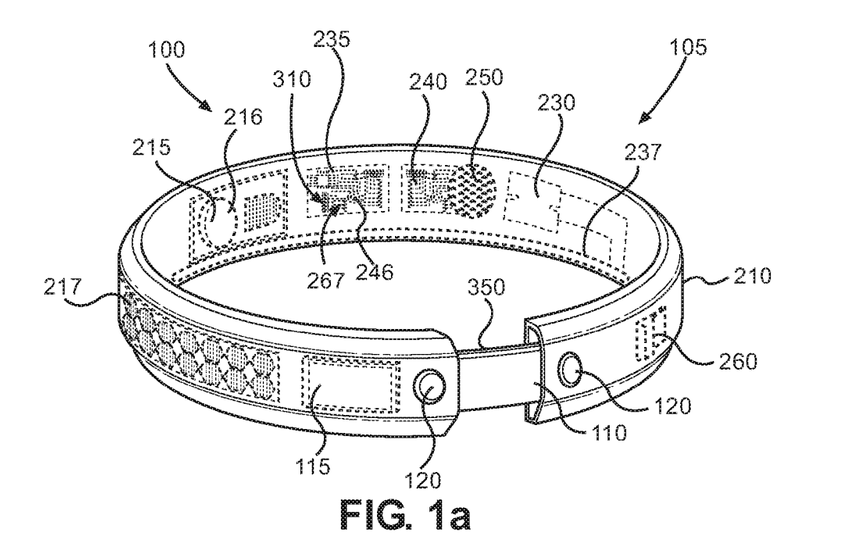
FIG. 1a shows a front perspective view illustrating a bracelet of the emergency services and information bracelet system according to an embodiment of the present invention.
Figure 1B:
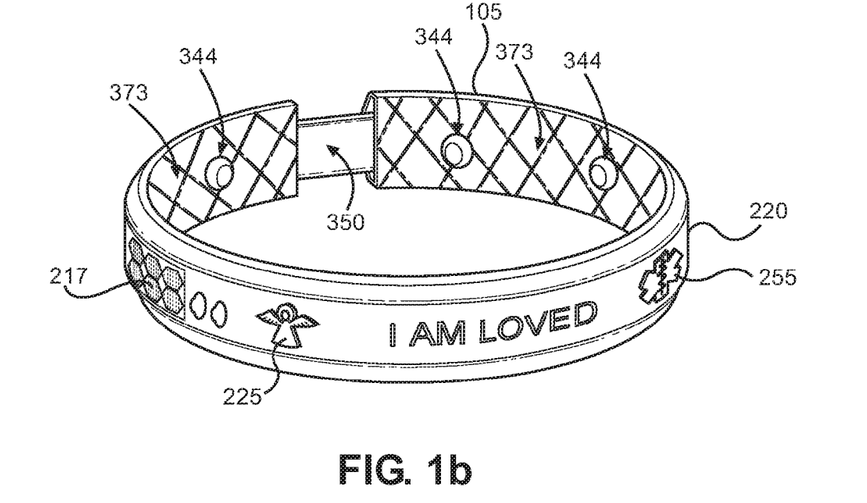
FIG. 1b shows a back perspective view illustrating a bracelet of the emergency services and information bracelet system according to an embodiment of the present invention.

Referring to the drawings by numerals of reference there is shown in FIG. 1a and FIG. 1b, front and back perspective views illustrating bracelet 105 of emergency services and information bracelet system 100 according to an embodiment of the present invention.

Emergency services and information bracelet system 100 has two embodiments. The emergency services and information bracelet system has more than one objective and multiple complimentary parts that work in conjunction with each other to achieve the objective. The first objective of this system is to identify the wearers of bracelet 105 as belonging to a family or group in the event of a catastrophe. It will provide emergency personnel with pertinent identifying information along with medical history and family contact information stored on fire and waterproof paper 110 within bracelet 105. Should a catastrophe or other emergency situation strike, bracelet 105 will ensure that family members or members of the group are found, identified, and properly treated right away.

For identification purposes, inside bracelet 105 would be the wearer's name, address, and phone number written on special paper, as well as any medical conditions and what types of medications, if any, are required, along with emergency contact information including an out of town contact. To assist in viewing this information, a small magnifying glass 115 would be provided. The information is included on fire and waterproof paper 110 so that emergency responders do not need to rely on technology, which may not be available due to a tragic event, in order to access the wearer's emergency information. Information can also be easily updated at any time. Importantly, with this information on paper, it could be instantly accessed, saving precious seconds or minutes. A unique safety lock design would be used to fasten bracelet 105 and hold the informative fire and waterproof paper 110 within the unit.

Figure 2:
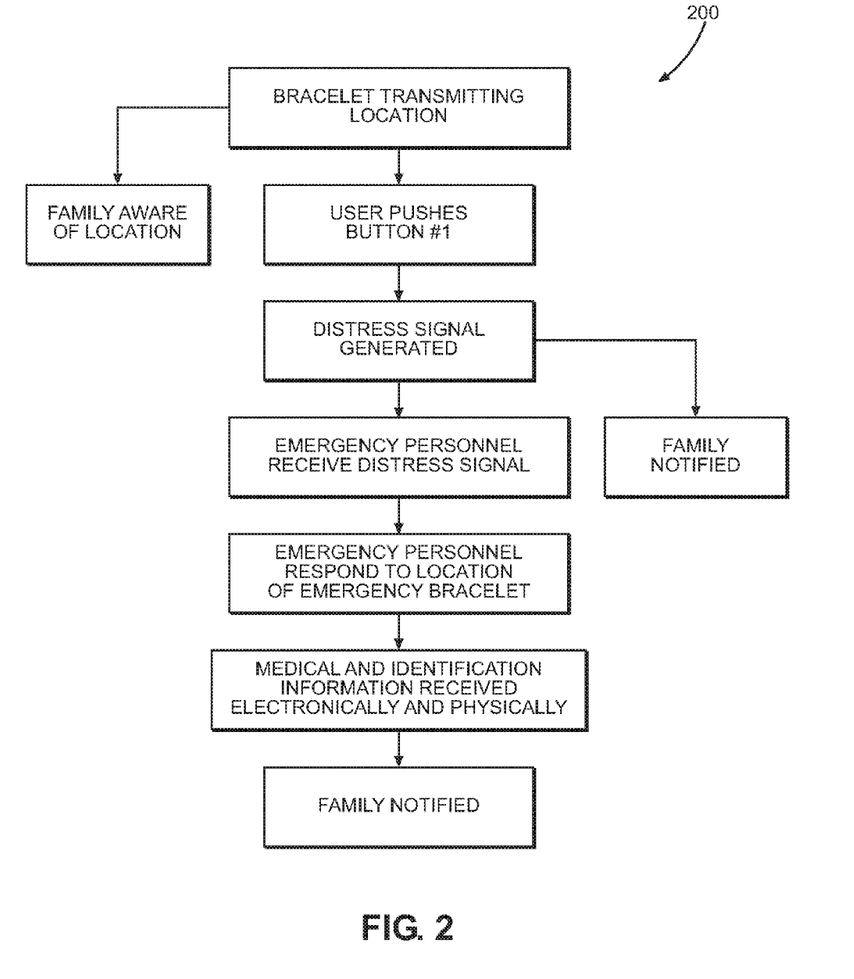
FIG. 2 is a chart illustrating a response sequence for a first embodiment of the emergency bracelet to be worn by a user for emergency services and information of the emergency services and information bracelet system according to an embodiment of the present invention of FIG. 1.

Referring now to FIG. 2, is a chart illustrating a response sequence for a first embodiment of emergency bracelet to be worn by a user for emergency services and information 200 of emergency services and information bracelet system 100 according to an embodiment of the present invention of FIG. 1.

The first embodiment of the emergency bracelet 105 comprises main body 210 that is adapted to wrap around and be maintained upon a user's wrist. Main body 210 is formed from a material that is waterproof and fireproof and has power source 215. Power source 215 is located and attached within main body 210 and power source 215 preferably includes battery member 216. Power source 215 may include solar panel 217 adapted to be attached to outer surface 220 of main body 210 and electrically attached to battery member 216 for recharging battery member 216.

First button 225 is attached to main body 210 and is adapted to activate GPS system 230 adapted to send location information wirelessly to emergency personnel and transmitter 235 is located and attached within main body 210 and is adapted to send information to GPS system 230. One example of an application for this system would be the ability of family members to be linked together so that parents are able to keep constant knowledge of the locations of their children through GPS system 230. Transmitter 235 includes frequency generator 246, amplifier 240, and internal antenna 237. Piece of paper 110 is adapted to be folded and stored within main body 210 and is capable of being retrieved by emergency personnel, and main body 210 contains vital information thereon about the user to be used by the emergency personnel to help aid the user in an emergency. Magnifying glass 115 is included and adapted to be stored within main body 210 and is capable of being retrieved by the emergency personnel to be used to read the vital information on piece of paper 110. Sound generator 250 is attached to main body 210 and is adapted to create a sound to indicate the need for emergency services.

There is second button 255 that is attached to main body 210 also that is adapted to activate sound generator 250. Emergency bracelet to be worn by a user for emergency services and information 200 further may comprise USB flash drive 260 adapted to be stored within main body 210 that is capable of being retrieved by the emergency personnel which contains vital information thereon about the user to be used by the emergency personnel to help aid the user in an emergency.

Figure 3:
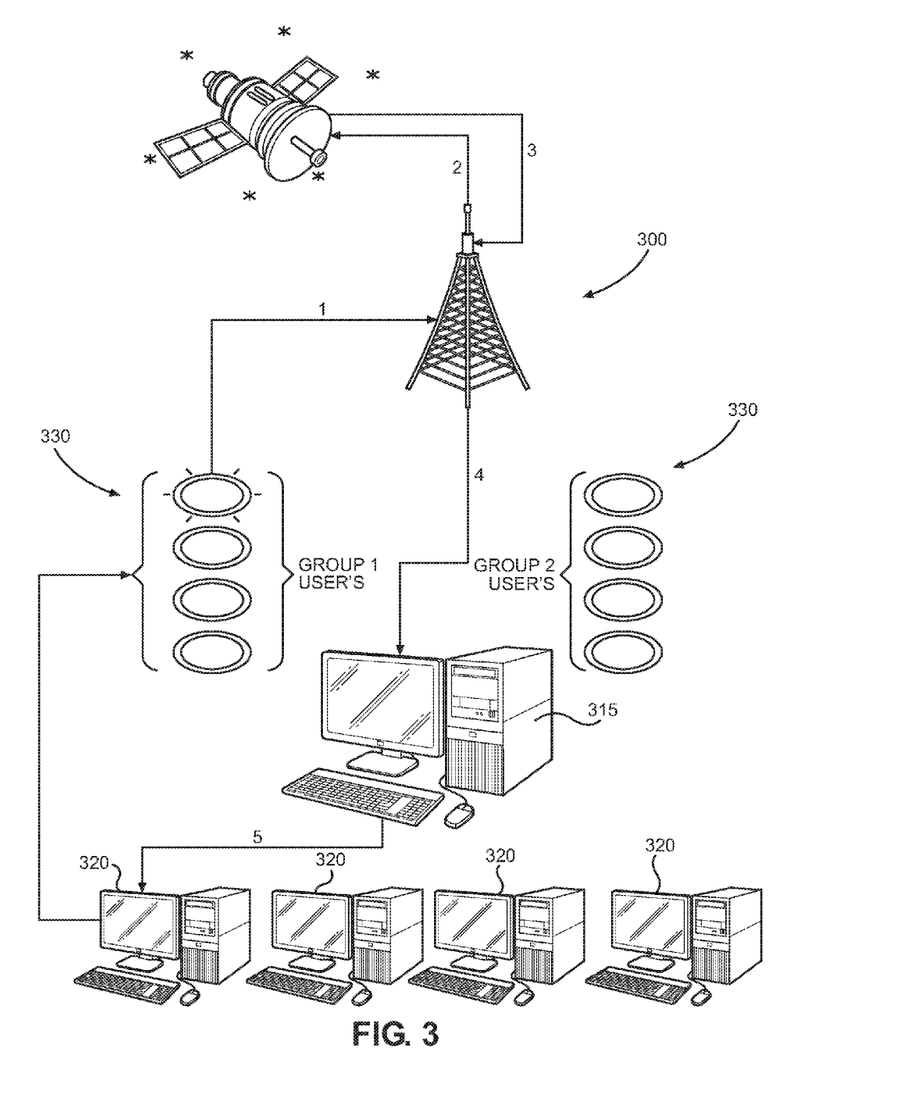
FIG. 3 is a diagram illustrating a response sequence for a second embodiment of the emergency bracelet to be worn by a user for emergency services and information of the emergency services and information bracelet system according to an embodiment of the present invention of FIG. 1.

Referring now to FIG. 3, is a diagram illustrating a response sequence for a second embodiment of emergency bracelet to be worn by a user for emergency services and information 200 of emergency services and information bracelet system 100 according to an embodiment of the present invention.

In the second embodiment, emergency system for emergency services 300 may comprise GPS system 230 and receiver unit 310 that is adapted to receive information from GPS system 230, central computer network 315 including at least one computer module 320 adapted to receive and process the information from receiver unit 310 and alert appropriate emergency personnel to user 330 at a location determined by GPS system 230 and an emergency bracelet 105 adapted to be worn by user 330 for providing emergency information. Computer module 320 includes multiple computer modules 320 adapted to link a plurality of users 330 together. The main body is adapted to wrap around and be maintained upon user's 330 wrist. Main body 210 is formed from a material that is adapted to be water proof and fireproof.

Power source 215 is located and attached within main body 210. Power source 215 includes battery member 216 but may also include solar panel 217 adapted to be attached to outer surface 220 of main body 210 and electrically attached to battery member 216 for recharging battery member 216. There is first button 225 that is attached to main body 210 that is adapted to activate GPS system 230 to send location information wirelessly to emergency personnel via transmitter 235. Transmitter 235 is located and attached within main body 210 and is adapted to send information to GPS system 230. Transmitter 235 includes frequency generator 246, amplifier 240, and internal antenna 237. Piece of paper 110 is adapted to be folded and stored within main body 210 and is capable of being retrieved by the emergency personnel and contains vital information thereon about user 330 to be used by the emergency personnel to help aid user 330 in an emergency.

Magnifying glass 115 is adapted to be stored within main body 210 and is capable of being retrieved by the emergency personnel to be used to read the vital information on piece of paper 110. Sound generator 250 is attached to main body 210 and is adapted to create a sound to indicate the need for emergency services. The second button 255 is attached to main body 210 and is adapted to activate sound generator 250. Emergency system for emergency services 300 may further comprise USB flash drive 260 adapted to be stored within main body 210 and is capable of being retrieved by the emergency personnel. USB flash drive 260 contains any necessary vital information thereon about user 330 that can be used by the emergency personnel to help aid user 330 in the event of an emergency.

Emergency services and information bracelet system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 4:
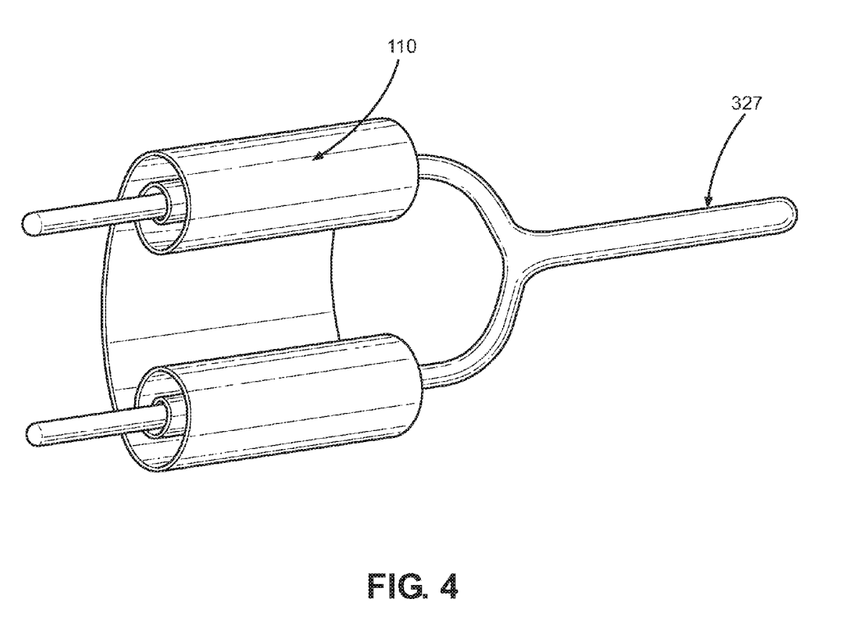
FIG. 4 shows a perspective view illustrating an alternate embodiment including a spindle member formed having a Y-shape and adapted to wrap informational pieces of paper there around to be stored within the bracelet.

Additional features, also shown in FIG. 1a, FIG. 1b, and FIG. 4 include a unique locking system is incorporated within the configuration of the main body of the emergency bracelet. The locking system includes a unique lock member 350 that is adapted to be connected to electric connectors 120 and wires within the main body. When the locking member is in a locked configuration these connectors 120 and wires will complete an electric circuit that will activate a green light to let the parents and all personnel on record know that the GPS system 230 is activated and working. If it is not locked it will not be activated and a red light will be activated and a signal will be sent to alert all personal on file within 30 seconds. The alert system can contact all personal contacts and include all emergency personnel. Further, the lock member 350 is attached to the main body and is adapted to releasably hold it upon the wrist of a person, and is adapted to send an electronic signal to the transmitter 235 when the emergency bracelet is disengaged from the locked configuration. Furthermore, the lock member 350 is adapted to send an electronic signal to the transmitter 235 when the lock member is located outside of a predetermined area. And as such, the transmitter 235 is adapted to send an emergency signal to emergency personnel when the emergency bracelet is located outside of said predetermined area.

Along with the unique lock member 350, computer circuitry 267 is embedded within the main body and includes software encoded thereon adapted to be programmed to define the predetermined area, such that when the emergency bracelet is located outside of the predetermined area the computer circuitry sends electronic signals to the transmitter, which in turn sends the emergency signal to the emergency personnel.

In an alternate embodiment, shown in FIG. 4, the emergency bracelet may further comprise a spindle member 327 formed having a Y-shape, is adapted to be stored within the main body, and is adapted to wrap the piece of paper 110 having the user's information there around, such that the piece of paper is rolled up, be accessible, and unrolled without being folded, wrinkled, or damaged such that when the emergency personnel access the piece of paper they can read information placed thereon. The spindle member 327 may look like a tuning fork. The waterproof and fireproof paper will wrap around the stems of the Y-shape and keep the important information completely organized.

Along with the GPS capabilities, the use of the internet and a website can also be incorporated to upload and download information per each individual bracelet. When information needs to be updated, for example a change of medication, address etc., a user can just access the dedicated website where each bracelet will come with their own access code and enter the new information. Then, a new unique lock will be sent and the user or their guardian will just replace the updated lock. The website would help parents or guardians to input online the perimeters of the predetermined area. If the user or child goes out of the predetermined area an alert gets sent to all authorized personnel with the user's or child's current GPS Location. The system can be activated by a cell phone, a computer, or even manually from the bracelet itself.

The emergency bracelet may further comprise pressure beads 344 attached to an outer surface of the main body that are adapted to press against a user's wrist and arm at specific pressure points and provide pressure to the wrist and arm during use. Some of these pressure points include "acupressure point H7" or "heart 7". The heart 7 is a functional acupressure point that is an effective solution to the problem of how to overcome anxiety, nervousness and palpitations naturally. This point is called the spirit gate and is found on the little finger side of the forearm at the wrist crease. This aids to treat emotional imbalances, nervousness, anxiety, palpitations, fear, and forgetfulness. In addition, it also helps to treat insomnia. Inserting a pressure bead 344 to align up to the wearers H7 acupressure point will help relieve and release stresses due to the sensory issues of the bracelet touching the skin.

Finally, the emergency bracelet may further comprise a shielding material 373 attached to an outer surface of the main body that is adapted to reside in between the main body and the wrist and arm of a user, and is adapted to shield radiation created by the emergency bracelet from radiating into the wrist and arm of said user. The shielding material 373 is also helpful to shield a user from radiation given off by the GPS System 230 within the bracelet. The shielding material can be formed from Shungite material. Shungite is considered as the miracle of health stone and is a unique black natural mineral. Shungite looks like coal and is a product related to amorphous carbon and graphite. Shungite is a mineral consisting of fine, disbursed globular-carbon in a crystalline phase and fullerenes. It absorbs substances from the environment, has bactericidal properties, and is highly adhesive (adhesion is the ability of dissimilar particles or services to cling to one another), and has radio screening abilities. Wearing Shungite accessories concentrates the health-giving energies and can eliminate things that can cause injuries to one's health. Shungite and Shungite accessories can shield a person from electro-magnetic radiation emitted By TV sets, computers, microwave ovens, mobile phones, and other sources of the EMR.

It should be noted that the steps described in the method of use can be carried out in many different orders according to user preference. The use of "step of" should not be interpreted as "step for", in the claims herein and is not intended to invoke the provisions of 35 U.S.C. § 112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claim:

1. An emergency bracelet to be worn by a user for emergency services and information, said emergency bracelet comprising:
   a main body;
      wherein said main body is adapted to wrap around and be maintained upon a user's wrist;
   a power source;
      wherein said power source is located and attached within said main body;
   a first button;
      wherein said first button is attached to said main body and is adapted to activate a GPS system adapted to send location information wirelessly to emergency personnel;
   a transmitter;
      wherein said transmitter is located and attached within said main body and is adapted to send information to said GPS system;

a piece of paper;
   wherein said piece of paper is adapted to be folded and stored within said main body and is capable of being retrieved by said emergency personnel; and
   wherein said piece of paper contains vital information thereon about said user to be used by said emergency personnel to help aid said user in an emergency;
a magnifying glass;
   wherein said magnifying glass is adapted to be stored within said main body and is capable of being retrieved by said emergency personnel to be used to read said vital information on said piece of paper;
a sound generator;
   wherein said sound generator is attached to said main body and is adapted to create a sound to indicate the need for emergency services;
a second button;
   wherein said second button is attached to said main body and is adapted to activate said sound generator;
a lock member including;
   wherein said lock member is attached to said main body and is adapted to releasably hold said emergency bracelet upon the wrist of a person;
   wherein said lock member is adapted to send an electronic signal to said transmitter when said emergency bracelet is disengaged from a locked configuration wherein said emergency bracelet can be removed from said person's wrist;
   wherein said lock member is adapted to send an electronic signal to said transmitter when said lock member is located outside of a predetermined area; and
   wherein said transmitter is adapted to send an emergency signal to emergency personnel when said emergency bracelet is located outside of said predetermined area; and
computer circuitry;
   wherein said computer circuitry is embedded within said main body and includes software encoded thereon adapted to be programmed to define said predetermined area, such that when said emergency bracelet is located outside of said predetermined area said computer circuitry sends electronic signals to said transmitter, which in turn sends said emergency signal to said emergency personnel.

2. The emergency bracelet of claim 1, wherein the transmitter includes a frequency generator, an amplifier, and an internal antenna.

3. The emergency bracelet of claim 1, wherein said main body is formed from a material that is waterproof.

4. The emergency bracelet of claim 1, wherein said main body is formed from a material that is fireproof.

5. The emergency bracelet of claim 1, further comprising a USB flash drive adapted to be stored within said main body and is capable of being retrieved by said emergency personnel; and
   wherein said USB flash drive contains vital information thereon about said user to be used by said emergency personnel to help aid said user in an emergency.

6. The emergency bracelet of claim 1, wherein said power source includes a battery member.

7. The emergency bracelet of claim 1, wherein said power source includes a solar panel adapted to be attached to an outer surface of said main body and electrically attached to said battery member for recharging said battery member.

8. An emergency system for emergency services comprising:
   a GPS system;
   a receiver unit including:
      wherein said receiver unit is adapted to receive information from said GPS system;
   a central computer network including:
      at least one computer module adapted to receive and process said information from said receiver unit and alert appropriate emergency personnel to a user at a location determined by said GPS system; and
      an internet website adapted to be accessed by a user to supply or retrieve information about a specific person, such that an emergency bracelet can be assigned to said specific person and said information about said specific person can be used to control said emergency bracelet, be used to provide emergency aid to said, specific person, and used to create a predetermined perimeter and area therein; and
   an emergency bracelet adapted to be worn by said user for providing emergency information, said emergency bracelet comprising:
      a main body;
         wherein said main body is adapted to wrap around and be maintained upon a user's wrist;
      a power source;
         wherein said power source is located and attached within said main body;
      a first button;
         wherein said first button is attached to said main body and is adapted to activate said GPS system to send location information wirelessly to emergency personnel;
      a transmitter;
         wherein said transmitter is located and attached within said main body and is adapted to send information to said GPS system;
      a piece of paper;
         wherein said piece of paper is adapted to be folded and stored within said main body and is capable of being retrieved by said emergency personnel; and
         wherein said piece of paper contains vital information thereon about said user to be used by said emergency personnel to help aid said user in an emergency;
      a magnifying glass;
         wherein said magnifying glass is adapted to be stored within said main body and is capable of being retrieved by said emergency personnel to be used to read said vital information on said piece of paper;
      a sound generator;
         wherein said sound generator is attached to said main body and is adapted to create a sound to indicate the need for emergency services;
      a second button;
      wherein said second button is attached to said main body and is adapted to activate said sound generator;
   a lock member including;
      wherein said lock member is attached to said main body and is adapted to releasably hold said emergency bracelet upon the wrist of a person;
      wherein said lock member is adapted to send an electronic signal to said transmitter when said emergency bracelet is disengaged from a locked configuration wherein said emergency bracelet can be removed from said person's wrist;

wherein said lock member is adapted to send an electronic signal to said transmitter when said emergency bracelet is located outside of said predetermined area; and wherein said transmitter is adapted to send an emergency signal to emergency personnel when said emergency bracelet is located outside of said predetermined area; and computer circuitry;

wherein said computer circuitry is embedded within said main body and includes software encoded thereon adapted to be programmed to define said predetermined area, such that when said emergency bracelet is located outside of said predetermined area said computer circuitry sends electronic signals to said transmitter, which in turn sends said emergency signal to said emergency personnel.

9. The emergency bracelet of claim 8, wherein the transmitter includes a frequency generator, an amplifier, and an internal antenna.

10. The emergency bracelet of claim 8, wherein said main body is formed from a material that is waterproof.

11. The emergency bracelet of claim 8, wherein said main body is formed from a material that is fireproof.

12. The emergency bracelet of claim 8, further comprising a USB flash drive adapted to be stored within said main body and is capable of being retrieved by said emergency personnel; and wherein said USB flash drive contains vital information thereon about said user to be used by said emergency personnel to help aid said user in an emergency.

13. The emergency bracelet of claim 8, wherein said power source includes a battery member.

14. The emergency bracelet of claim 8, wherein said power source includes a solar panel adapted to be attached to an outer surface of said main body and electrically attached to said battery member for recharging said battery member.

15. The emergency bracelet of claim 8, wherein said at least one computer module includes a plurality of computer modules adapted to link a plurality of users together.

16. The emergency bracelet of claim 1, further comprising a spindle member formed having a Y-shape, is adapted to be stored within said main body, and is adapted to wrap said piece of paper there around, such that said piece of paper is rolled up, be accessible, and unrolled without being folded, wrinkled, or damaged such that when said emergency personnel access said piece of paper they can read information placed thereon.

17. The emergency bracelet of claim 1, further comprising pressure beads attached to an outer surface of said main body that are adapted to press against a user's wrist and arm and provide pressure to said wrist and arm during use.

18. The emergency bracelet of claim 1, further comprising a shielding material attached to an outer surface of said main body that is adapted to reside in between said main body and the wrist and arm of a user, and adapted to shield radiation created by said emergency bracelet from radiating into said wrist and arm of said user.

19. The emergency bracelet of claim 18, wherein said shielding material is formed from Shungite material.

20. The emergency bracelet of claim 8, further comprising a spindle member formed having a Y-shape, is adapted to be stored within said main body, and is adapted to wrap said piece of paper there around, such that said piece of paper is rolled up, be accessible, and unrolled without being folded, wrinkled, or damaged such that when said emergency personnel access said piece of paper they can read information placed thereon; pressure beads attached to an outer surface of said main body that are adapted to press against a user's wrist and arm and provide pressure to said wrist and arm during use; a shielding material attached to an outer surface of said main body that is adapted to reside in between said main body and the wrist and arm of a user, and adapted to shield radiation created by said emergency bracelet from radiating into said wrist and arm of said user; and wherein said shielding material is formed from Shungite material.

* * * * *